United States Patent [19]
Hoffer

[11] Patent Number: 4,636,210
[45] Date of Patent: Jan. 13, 1987

[54] MULTI-PART INTRAOCULAR LENS AND METHOD OF IMPLANTING IT IN AN EYE

[76] Inventor: Kenneth J. Hoffer, 1407 Georgina Ave., Santa Monica, Calif. 90402

[21] Appl. No.: 806,542

[22] Filed: Dec. 9, 1985

[51] Int. Cl.⁴ .............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,056,855 | 11/1977 | Kelman | 623/6 |
| 4,092,743 | 6/1978 | Kelman | 623/6 |
| 4,174,543 | 11/1979 | Kelman | 623/6 |
| 4,268,921 | 5/1981 | Kelman | 623/6 |
| 4,296,501 | 10/1981 | Kelman | 623/6 |
| 4,343,050 | 8/1982 | Kelman | 623/6 |
| 4,370,760 | 2/1983 | Kelman | 623/6 |
| 4,451,938 | 6/1984 | Kelman | 623/6 |
| 4,476,591 | 10/1984 | Arnott | 623/6 |
| 4,573,998 | 3/1986 | Mazzocco | 623/6 |

FOREIGN PATENT DOCUMENTS 2124500 2/1984 United Kingdom .................... 623/6

OTHER PUBLICATIONS

Kelman, Intraocular Lens and Method of Inserting an Intraocular Lens in an Eye, published EPO Application No. 0 099 641, filed Jun. 14, 1983, published Feb. 1, 1984.

*Primary Examiner*—Ronald L. Frinks
*Attorney, Agent, or Firm*—Pretty, Schroeder, Brueggemann & Clark

[57] ABSTRACT

A multi-part intraocular lens that can be surgically implanted within an eye through an incision having a length substantially less than the lens' diameter. The lens includes a plurality of lens segments that are slidable between a retracted orientation, in which they cooperate to form a generally circular lens, and an extended orientation, in which they cooperate to form an elongated assembly having a transverse width substantially less than the lens' diameter. To surgically implant the lens, it is inserted through the eye incision in the extended orientation, whereupon further insertion causes the lens segments to slide to their retracted orientation automatically, without the need for a risky assembly of segments using surgical instruments within the eye.

20 Claims, 7 Drawing Figures

MULTI-PART INTRAOCULAR LENS AND METHOD OF IMPLANTING IT IN AN EYE

BACKGROUND OF THE INVENTION

This invention relates generally to intraocular lenses, and, more particularly, to multi-part intraocular lenses that can be surgically implanted in an eye through an incision that is smaller than the diameter of the lens' optic.

In the human eye, the crystalline lens is situated behind the pupil and iris and it functions to focus light entrant through the cornea and pupil onto the retina at the rear of the eye. The lens is a biconvex, highly transparent structure made of slender, curved rod-shaped ectodermal cells in concentric lamellae surrounded by a thin capsule. The lens capsule is supported at its periphery by suspensory ligaments, called zonules, that are continuous with the ciliary muscle.

A cataract condition results when the material within the lens capsule becomes clouded, thereby obstructing the passage of light. To correct this condition, two forms of surgery are used. In intracapsular cataract extraction, the entire lens is removed intact. To accomplish this, the surgeon severs the zonules or suspensory ligaments about the entire periphery of the capsule, and removes the entire lens with the capsule and its content material intact.

In extracapsular cataract extraction, an incision is made through the front wall (i.e., the anterior capsule) of the lens, and the clouded cellular material within the capsule is removed through this opening. Various techniques are used to accomplish this removal. The transparent rear capsule wall (i.e., the posterior capsule), as well as the zonules and peripheral portions of the anterior capsule (i.e., the anterior capsule flaps), all remain in place in the eye.

Both intracapsular and extracapsular extraction eliminate the light blockage due to the cataract. However, the light now entrant through the cornea and pupil is unfocused since there is no longer a lens in the eye. Appropriate focusing can be achieved by a lens (i.e., a contact lens) exterior to the eye. This approach, though generally satisfactory, has the disadvantage that when the external contact lens is removed, the patient effectively has no useful sight. A preferred alternative is to implant an artificial, intraocular lens directly within the eye. The lens is implanted through an incision made near the periphery of the cornea.

The length of the incision in the eye is an important factor in determining the rate of healing following lens implantation. A longer incision usually means longer post-operative recovery and healing periods for the patient. Other problems associated with lengthy incisions include expulsive hemorrhage, iris prolapse, bleb formation and high astigmatism. Accordingly, it is desirable to reduce the length of the incision as much as possible.

There have been several efforts in the past to reduce incision length by specially configuring the intraocular lens. In one such effort, the lens includes separable elements that are inserted individually into the eye and then connected together using surgical tools. These separate lens elements may include portions of the lens body itself, as well as position-fixation haptics or loops projecting outwardly from the lens body to center the lens within the eye. Using this technique, it is possible for the incision length to be smaller than the final diameter of the lens body or optic.

Although the individual insertion of separable lens elements permits use of a smaller incision, it necessarily requires the use of surgical tools within the eye, to assemble the elements together. This increases the risk of accidentally touching and irreparably injuring the eye's cornea, iris or capsule. In addition, the necessity of separately inserting and connecting together a number of lens elements within the eye complicates an already delicate positioning procedure.

Another lens that can be implanted through an incision smaller than the final diameter of the lens body includes a central lens member and two side lens members hinged to opposite sides of the central member. The side members pivot about axes in the plane of the central member. In use, the lens members are folded together for insertion into the eye through a relatively small incision and are then unfolded using a suitable tool, to produce a generally circular lens. The unfolding of the lens elements within the eye risks accidentally touching and irreparably injuring the eye's cornea, iris and capsule.

Still another lens that can be implanted through an incision smaller than the final diameter of the lens body is constructed of a transparent material that is highly flexible, such as silicone. Such lenses are folded for insertion through a small incision, and then unfolded into their final shape within the eye. Again, the unfolding within the eye risks injury to the cornea, iris and capsule. In addition, it is preferred to use harder and less flexible lens materials such as polymethyl methacrylate, which have been used successfully for decades.

It should therefore be appreciated that there has existed a definite need for an intraocular lens capable of being inserted into an eye through an incision having a length smaller than the lens' diameter, without increasing the risk of accidental eye injury and without requiring the use of highly flexible materials such as silicone. The present invention fulfills this need.

SUMMARY OF THE INVENTION

The present invention is embodied in a multi-part intraocular lens having a plurality of lens segments that are slidably attached to each other in such a way that the lens can be inserted into an eye through an incision that is smaller than the final diameter of the lens body or optic. As the lens is inserted through the incision, its separate segments automatically slide together to form a substantially circular optical lens that can be properly centered within the eye. This lens configuration permits its surgical implantation through an incision of substantially reduced length, which shortens the healing process and obviates certain problems associated with lengthy incisions. In addition, because the separate lens segments slide together automatically during insertion, the lens configuration obviates the need for performing complex and dangerous manipulations of separate lens segments within the eye.

More particularly, the intraocular lens of the present invention includes a plurality of lens segments and lens guiding means for slidably attaching the lens segments to each other. The lens segments are slidable between a retracted orientation, in which the segments cooperate to form a lens optic having a first predetermined transverse width, and an extended orientation, in which the segments form an elongated shape having a maximum transverse width substantially less than the lens optic's first predetermined transverse width. The lens can thereby be inserted into the eye through an incision of substantially reduced length.

To insert the lens, the plurality of lens segments are initially slid to the elongated, extended orientation. One end of the elongated assembly is then inserted through the incision until it engages a predetermined portion of the eye (e.g., the ciliary sulcus, capsule equator or anterior chamber angle), to inhibit further movement of that leading end. Further insertion causes the remaining lens segments to pass through the incision and slide relative to the preceding segments and thus move into the retracted orientation. The lens then may be centered in its final position within the eye using a plurality of position-fixation haptics or loops projecting outwardly from the lens segments.

In a more detailed aspect of the invention, the plurality of lens segments are contiguous and non-overlapping when in the retracted orientation and the lens guiding means is carried on the segments' contiguous edges. The lens guiding means preferably includes a tongue and mating groove extending along the contiguous edges, such that the segments are conveniently slidable relative to each other. The tongue and groove are preferably configured such that they are in intimate contact with each other, to minimize undesired refraction at the interface. In addition, the lens guiding means preferably includes means for preventing the contiguous lens segments from detaching from each other during normal use, as well as means for preventing the segments from sliding beyond their desired, final positions.

In one preferred form of the invention, the plurality of lens segments include a primary lens segment forming a central portion of the lens and first and second secondary lens segments located on opposite sides of the primary lens segment. A position-fixation loop is preferably attached to each of the secondary lens segments. Thus, the leading end of the lens, which is inserted first through the incision during surgical implantation, is defined by the loop attached to the first secondary lens segment. Movement into the eye of the leading end loop, and the first secondary lens element to which it is attached, is inhibited when the loop engages the predetermined portion of the eye's interior, e.g., the ciliary sulcus. Further insertion of the lens through the incision causes the primary lens segment and the second secondary lens segment to slide into the retracted orientation. The loop attached to the second secondary lens segment is the final portion of the lens to pass through the incision.

The secondary lens segments may advantageously be of substantially equal size and be shaped substantially like lunar crescents. The primary lens segment thus is widest at its midpoint. This maximum width is preferably about one-half the lens' final diameter. The lens elements are thus sized such that, when the lens is properly centered in the eye and when normal lighting conditions are present, the pupil of the eye transmits light through only the primary lens segment. This eliminates the occurrence of any optical distortion that might unexpectedly be caused by light passing through the lens guiding means carried on the contiguous edges of the lens segments.

Other features and advantages of the present invention will become apparent from the following description of the preferred embodiments, taken in conjunction with the accompanying drawings, which illustrate, by way of example, the principles of the invention.

BRIEF DESCRIPTION OF THE DRAWINGS

The accompanying drawings illustrate the invention. In such drawings.

DESCRIPTION OF THE PREFERRED EMBODIMENTS

Figure 1:
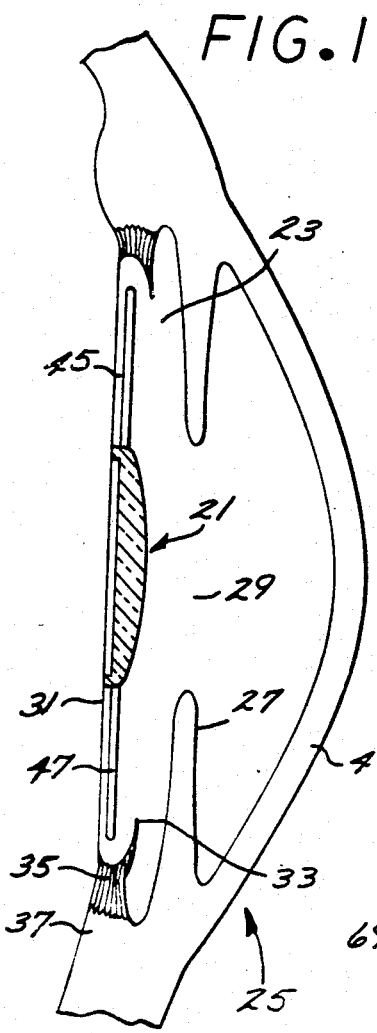
FIG. 1 is a side sectional view of an intraocular lens implanted in an eye.

With reference now to the exemplary drawings, and particularly to FIG. 1, there is shown an intraocular lens 21 surgically implanted in the posterior chamber 23 of a human eye 25, behind the eye's iris 27 and pupil 29. The depicted lens has been implanted as a replacement for the eye's natural lens, which was extracted because of a cataract condition. In such an extraction, a small incision is made through the natural lens' front wall or anterior capsule and the clouded cellular material within the capsule is removed, for example, by suction. Remaining behind are the natural lens' rear wall or posterior capsule 31 as well as the peripheral portions or flaps 33 of the anterior capsule and zonules 35 for attaching the capsule to the eye's ciliary muscle 37.

Figure 2:
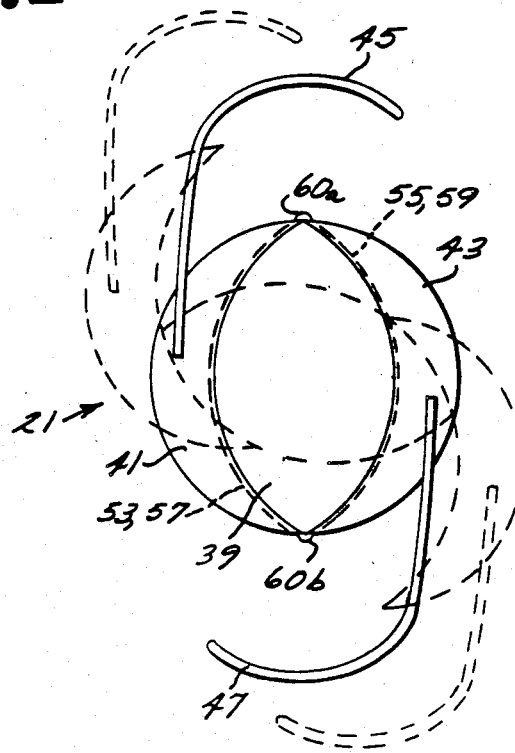
FIG. 2 is a plan view of a first intraocular lens embodiment of the invention, with dotted lines showing the lens in an extended orientation suitable for insertion into an eye and with solid lines showing the lens in a retracted orientation after insertion.

FIG. 2 is a plan view of a first embodiment of the intraocular lens 21 of the invention. The lens includes a primary or central lens segment 39 and two secondary or lateral lens segments 41 and 43 attached to opposite sides of the central segment. The central segment is shaped generally like the longitudinal cross-section of an American football or oblong with opposite side edges having the same, uniform radius. The lateral segments are formed as first and second lateral lens segments 41 and 43 shaped substantially like lunar crescents of the same size having concave edges that are comformable with the opposite side edges of the central lens segment 39. The three segments together form a circular lens having any desired optical power. As is conventional, the lens may be plano-convex, biconvex or convexo-concave. Resilient position-fixation haptics or loops project outwardly from the lens segments, for use in centering and retaining the lens in its desired position within the eye 25. In FIG. 2, two such loops 45 and 47 are shown projecting outwardly from the lateral lens segments 41 and 43, respectively.

The implanted lens 21 is inserted through an incision (not shown) near the periphery of the eye's cornea 49. The pupil 29 is ordinarily dilated, to facilitate placement of the lens behind it, in the posterior chamber 23. Alternatively, the lens may be implanted in front of the pupil, in the anterior chamber 50. The corneal incision through which the lens 21 is inserted during implantation is preferably made as short as possible, to quicken its healing. Most prior lens configurations, however, prevent a reduction of the incision length to less than the diameter of the lens optic.

In accordance with the present invention, the three lens segments 39, 41 and 43 are slidable relative to each other in such a way that the lens can be configured into an elongated orientation having a transverse width substantially less than the diameter of the lens optic (when in its circular orientation). The lens can thereby be surgically implanted through an incision of substantially reduced length. As the lens is inserted through the incision, its separate segments slide together automatically to form the generally circular lens, without ordinarily requiring the insertion into the eye of any surgical instruments for assembling the segments together. The use of such instruments might be required in some limited circumstances. The lens can thereby be implanted with minimal risk of injury to the eye.

The three lens segments 39, 41 and 43 are preferably attached to each other by a tongue-and-groove mechanism that permits them to slide along their contiguous edges. In a retracted orientation (solid lines in FIG. 2), the lens segments cooperate to form a generally circular lens, while in an extended orientation (dotted lines in FIG. 2), the lens segments form an elongated shape having a transverse width substantially less than the final diameter of the lens optic. In the extended orientation, the position-fixation loops 45 and 47 project outwardly from the lens' two ends.

Figure 4:
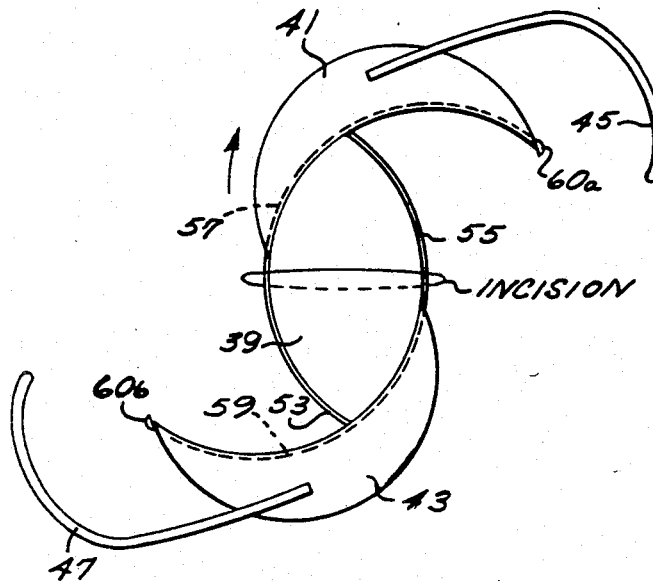
FIGS. 4-6 are plan views of the lens of FIG. 2 showing progressions in orientation of the lens segments as they are surgically inserted through an incision in an eye.
Figure 5:
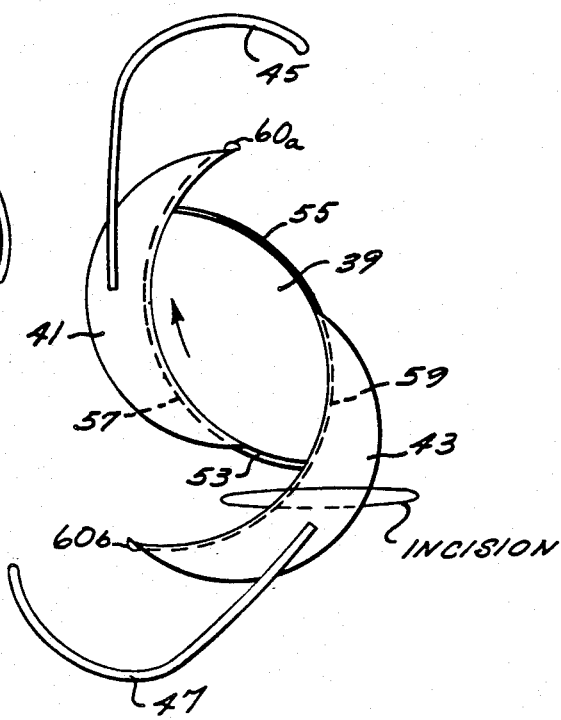
Figure 6:
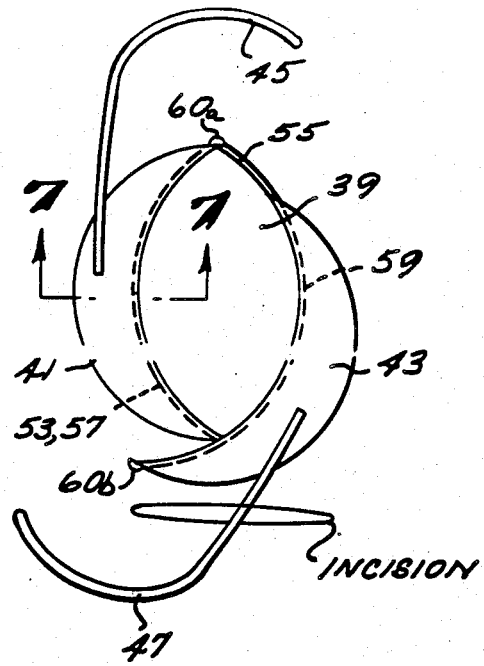

FIGS. 4-6 are a sequence of views depicting the lens embodiment 21 of FIG. 2 as it is being surgically implanted into an eye through an incision depicted schematically at 51. In FIG. 4 the three lens segments 39, 41 and 43 have been slid to the fully extended orientation and the position-fixation strand 45 and lateral lens segments 41 at one end of the elongated assembly have been inserted through the incision. In particular, the lens has been inserted to the point where the leading loop 45 contacts a predetermined portion of the eye's interior (e.g., the ciliary sulcus, the capsule equator, or the anterior chamber angle), which limits further inward movement of both the loop 45 and the lateral lens segment 41 to which it is attached.

Continued insertion of the trailing lens segments 39 and 43 and trailing loop 47 cause the central segment 39 to slide relative to the leading segment 41, whose movement is being resisted. FIG. 5 depicts the lens configuration after the central segment has slid a substantial distance in this fashion.

After the central lens segment 39 has slid to its fully retracted position relative to the leading lateral lens segment 41, continued insertion of the trailing lateral lens segment 43 and trailing loop 47 causes the latter segment to slide relative to the center segment. FIG. 6 depicts the lens configuration after this trailing segment 43 has slid a substantial distance in this fashion.

Still further insertion causes the trailing segment 43 to slide to its fully retracted position, after which time the lens can be properly centered within the eye 25. This centering is ordinarily accomplished by placing the position-fixation loops 45 and 47 into the cleft or fornix of the lens capsule, the ciliary sulcus, or the anterior chamber angle. The resilience of the loops functions to align the lens with the center of the pupil 29.

It will be appreciated that throughout the insertion procedure, the transverse width of the portion of the lens passing through the incision 51 is substantially less than the lens optic's final diameter. This permits use of an incision of substantially reduced length, which correspondingly reduces the time required for the wound to heal. In the embodiment of FIGS. 2 and 4-6, for example, the maximum transverse width of the lens during insertion through the incision is only about one-half the lens optic's final diameter. This permits the incision length to be reduced to about one-half its normal size.

It will also be appreciated that the lens segments 39, 41 and 43 slide together into their final circular configuration automatically, usually without the need to insert any surgical tools within the eye 25 and without moving the lens segments out of a generally coplanar relationship. This significantly reduces the risk of accidentally injuring the eye, particularly the cornea 49, iris 27 and posterior capsule 31.

As previously mentioned, the lens segments 39, 41 and 43 are slidably attached to each other by a tongue and mating groove mechanism. In particular, the center segment 39 includes elongated tongues 53 and 55 on its opposite edges, and the respective lateral segments 41 and 43 include mating grooves 57 and 59 on their inwardly-facing edges. Small beads 60a and 60b located at the remote ends of the lens segments 41 and 43, respectively, prevent the segments from sliding beyond their desired final positions.

Figure 7:
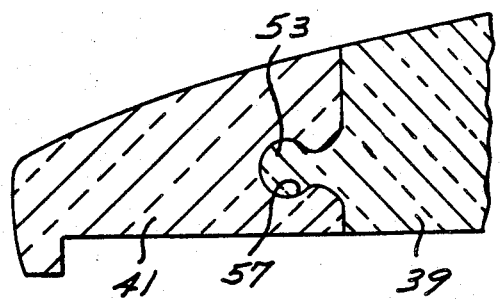
FIG. 7 is a cross-sectional diagram of a tongue and mating groove assembly for attaching together the various lens segments of the embodiments of FIGS. 2 and 3, while permitting the lens segments to slide relative to each other.

FIG. 7 is a cross-sectional view of the lens 21, depicting the conforming shapes of the tongue 53 and groove 57. It will be observed that the groove is undercut, to hold the lens segments 39 and 41 tightly together and prevent their separation. The tongue and mating groove are preferably configured to minimize the existence of any air gaps between them. Any such air gaps could cause undesired refraction of light passing through the lens. In addition, forming the separate lens segments of the same material, for example, polymethyl methacrylate, minimizes undesired refraction and reflection at the interfaces between the tongue and groove caused by differences in refractive indices.

Forming the center lens segment 39 in the general shape of the longitudinal cross-section of an American football and the lateral lens segments 41 and 43 in the general shape of a lunar crescent provides the lens 21 with an important advantage. When the lens is properly implanted in its desired position within the eye 25, the pupil 29 is normally sized to transmit light only to the center lens segment 39. Only in very low-light conditions does the pupil size increase sufficiently to permit light to pass through the lateral lens segments 41 and 43 and thus the tongue and groove interfaces between the segments. Even then, only a small proportion of the light passes through the tongue and groove interfaces. This minimizes any undesired optical effects the interfaces might provide.

Figure 3:
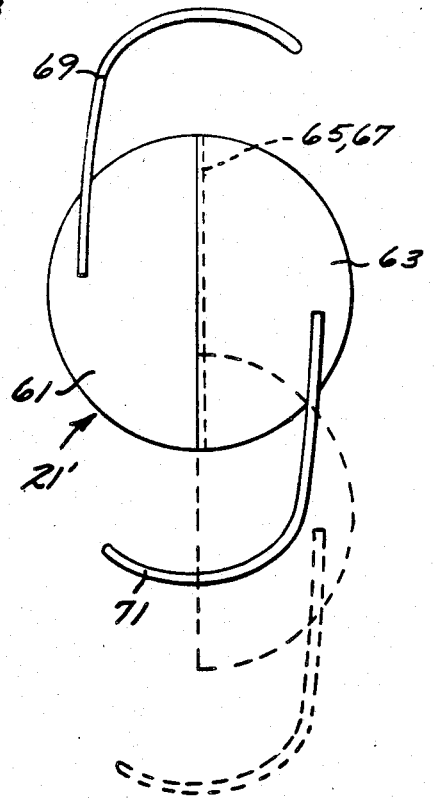
FIG. 3 is a plan view of a second intraocular lens embodiment of the invention, with dotted lines showing the lens in its extended orientation and solid lines showing the lens in its retracted orientation.

An alternative embodiment of the intraocular lens of the present invention is depicted in FIG. 3. In this embodiment, the lens 21' includes two half-circular lens segments 61 and 63 that together form a circular lens having any desired optical power. As with the lens embodiment of FIG. 2, the lens segments of this embodiment include a tongue 65 and mating groove 67 that permit the segments to slide between a retracted orientation, in which the lens is circular, and an extended orientation, in which the lens is elongated and has a transverse width substantially less than its circular diameter. Resilient haptics or loops 69 and 71 project outwardly from the respective lens segments 61 and 63, for use in centering the lens within the eye 25.

The lens 21' of FIG. 3 is surgically implanted in the eye in substantially the same fashion as the lens 21 of FIG. 2, as described above. Here, however, there is sliding between merely two lens segments rather than three. More particularly, the lens is first slid to its extended orientation (dotted lines in FIG. 3) and one end is then inserted through the eye incision. Insertion continues until the leading strand 69 contacts a predetermined portion of the eye's interior (e.g., the ciliary sulcus, capsule equator, or anterior chamber angle), which limits further inward movement. Continued inserted causes the trailing lens segment 63 to slide relative to the leading lens segment 61, until the lens has slid to its retracted orientation (solid lines in FIG. 3). The lens can then be properly centered within the eye by means of the resilient loops 69 and 71. Using this implantation procedure, the lens 21' can be inserted through an incision substantially smaller than its final diameter and can be properly placed in its final circular orientation without ordinarily requiring the insertion of any special surgical instruments within the eye.

It should be appreciated from the foregoing description that the present invention provides a multi-part intraocular lens that can be surgically implanted within an eye through an incision having a length substantially less than the lens' final diameter, without the need for a risky assembly of individual lens components within the eye. The lens includes a plurality of segments that are slidably attached to each other such that the lens can be slid to an elongated orientation for insertion into the eye. As the lens in inserted through a small incision into the eye, its separate segments slide together automatically to form the lens optic's final circular shape.

Although the invention has been described in detail with reference to the presently preferred embodiments, those of ordinary skill in the art will appreciate that various modifications can be made without departing from the invention. Accordingly, the invention is limited only by the following claims.

I claim:

1. An intraocular lens comprising:
   a plurality of lens segments; and
   lens guiding means for slidably attaching said plurality of lens segments to each other, such that said lens segments are slidable between a retracted orientation, in which said lens segments cooperate to form an optical lens having a first predetermined transverse width, and an extended orientation, in which said lens segments have a second predetermined transverse width, substantially less than the first predetermined transverse width;
   wherein when said lens segments are positioned in the extended orientation, they are insertable into an eye through an incision having a length that is less than the first predetermined transverse width of said lens, after which the lens segments can be slid to the retracted orientation for proper positioning within the eye.

2. An intraocular lens as recited in claim 1, wherein:
   when said plurality of lens segments are in the retracted orientation, the segments are contiguous and non-overlapping; and
   said lens guiding means is carried on the contiguous edges of said plurality of lens segments.

3. An intraocular lens as recited in claim 2, wherein said lens guiding means includes an elongated tongue located on the contiguous edge of one of said lens segments and a mating, elongated groove located on the contiguous edge of another of said lens segments, whereby said lens segments are slidable relative to each other.

4. An intraocular lens as recited in claim 2, wherein said lens guiding means includes means for preventing said plurality of lens segments from detaching from each other during normal use.

5. An intraocular lens as recited in claim 1, wherein the second predetermined transverse width of said lens is about one-half the first predetermined transverse width of said lens.

6. An intraocular lens as recited in claim 1, wherein said plurality of lens segments include a primary lens segment forming the central portion of said lens and first and second secondary lens segments located on opposite sides of said primary lens segment.

7. An intraocular lens as recited in claim 6, wherein said first and second secondary lens segments are of substantially equal size and are shaped substantially like lunar crescents.

8. An intraocular lens as recited in claim 7, wherein said plurality of lens segments are sized and configured such that, when said plurality of lens segments are in the retracted orientation and said lens is properly centered within the eye and when normal lighting conditions are present, the pupil of the eye transmits light passing only through said primary lens segment.

9. An intraocular lens as recited in claim 6, and further including first and second position-fixation haptics connected to said respective first and second secondary lens segments and adapted to center said lens within the eye.

10. An intraocular lens as recited in claim 1, wherein said plurality of lens segments includes first and second lens segments of substantially equal size, each lens segment having a substantially semicircular shape.

11. A method of inserting and positioning an intraocular lens within an eye, said lens having a plurality of lens segments and lens guiding means for slidably attaching the lens segments to each other such that the segments are slidable between a retracted orientation, in which the segments cooperate to form an optical lens having a first predetermined transverse width, and an extended orientation, in which the segments have a second predetermined transverse width, substantially less than the first predetermined transverse width, whereby the lens segments can be inserted into an eye through an incision substantially less than the lens' first predetermined transverse width, said method comprising steps of:
   sliding said lens segments to the extended orientation;
   inserting a leading end of said lens through an incision in the eye until such leading end engages a predetermined portion of the eye, to inhibit further movement of the leading end;
   inserting further portions of the lens through the incision such that the plurality of lens segments slide to the retracted orientation; and
   centering said lens within the eye.

12. A method as recited in claim 11, wherein:
   the lens further includes first and second position-fixation haptics attached to lens segments at opposite ends of the lens when the lens is in the extended orientation;

the first position-fixation haptic forms the leading end of the lens that is inserted through the incision in said step of inserting; and the predetermined portion of the eye that is engaged by the first haptic of the lens is the ciliary sulcus, capsule equator, or anterior chamber angle, such engagement inhibiting further inward movement of both the first haptic and the lens segment to which it is attached.

13. A method as defined in claim 12, wherein:

the lens includes a primary lens segment and first and second secondary lens segments slidably attached to opposite sides of the primary lens segment;

the first and second position-fixation haptics are attached to the first and second secondary lens segments respectively; and said step of inserting further portions of the lens includes steps of
inserting the primary lens segment through the incision,
inserting the second secondary lens segment through the incision, and
inserting the second haptic through the incision, such that the lens segments are automatically slid to the retracted orientation.

14. A method as defined in claim 13, wherein said steps of inserting are ordinarily all performed without positioning any tools within the eye.

15. An intraocular lens comprising:

a central lens segment having an oblong shape with opposite side edges having the same, uniform radius; and first and second lateral lens segments of substantially the same size and shaped substantially like lunar crescents, the first and second lateral lens segments further having concave edges conformable with the opposite side edges of the center lens segment; and means for attaching said first and second lateral lens segments to said central lens segment, with the respective concave edges of the first and second lateral segments conformably engaging the opposite side edges of the center lens segment;

wherein said lens segments are sized such that when the lens is properly implanted within a human eye, and when normal lighting conditions are present, the eye's pupil transmits light only through the central lens segment.

16. An intraocular lens as recited in claim 15, wherein said means for attaching includes an elongated tongue and a mating elongated groove carried by the contiguous edges of said center lens segment and said first and second lateral lens segments, the tongue and groove allowing sliding relative movement of the lens segments between a retracted orientation, in which the lens segments cooperate to form a generally circular lens having a predetermined diameter, and an extended orientation, in which the lens elements cooperate to form an elongated assembly having a transverse width substantially less than the predetermined diameter.

17. An intraocular lens as defined in claim 16, and further including first and second position-fixation haptics projecting outwardly from the respective first and second lateral lens segments and adapted to center the lens within the eye.

18. An intraocular lens as defined in claim 16, wherein the maximum transverse width of the intraocular lens in its extended orientation is about one-half the lens' predetermined diameter.

19. An intraocular lens as defined in claim 15, wherein the opposite side edges of said center lens segment define substantially its entire peripheral edge.

20. An intraocular lens comprising:

a primary lens segment having a peripheral edge defined by first and second edges having the same, uniform curvature;

first and second secondary lens segments of substantially the same size, each secondary lens segment being shaped substantially like a lunar crescent with a concave edge and a convex edge, the concave edge being conformable with a respective one of the first and second edges of the primary lens segment;

first tongue and undercut groove means carried by the first edge of the primary lens segment and the concave edge of the first secondary lens segment, for slidably attaching the respective lens segments together;

second tongue and undercut groove means carried by the second edge of the primary lens segment and the concave edge of the second secondary lens segment, for slidably attaching the respective lens segments together; and first and second resilient, position-fixation haptics attached to, and projecting outwardly from, the respective first and second secondary lens segments;

wherein the primary and secondary lens segments are slidable relative to each other between a retracted orientation, in which they cooperate to from a substantially circular optical lens having a predetermined diameter, and an extended orientation, in which they cooperate to form an elongated assembly with a predetermined width substantially less than the diameter;

and wherein when the primary and secondary lens segments are positioned in the extended orientation, the lens is insertable into an eye through an incision having a length substantially less than the lens' predetermined diameter, after which the lens segments can be slid to the retracted orientation for proper positioning within the eye.

* * * * *